(12) United States Patent
Crepeau

(10) Patent No.: US 7,081,248 B2
(45) Date of Patent: Jul. 25, 2006

(54) CONCENTRATED WATER-DISPERSIBLE VITAMIN COMPOSITIONS

(75) Inventor: Michel Andre Crepeau, Pueblo West, CO (US)

(73) Assignee: Adisseo France S.A.S. (FR)

( * ) Notice: Subject to any disclaimer, the term of this patent is extended or adjusted under 35 U.S.C. 154(b) by 0 days.

(21) Appl. No.: 09/920,365

(22) Filed: Aug. 3, 2001

(65) Prior Publication Data

US 2003/0078243 A1  Apr. 24, 2003

(51) Int. Cl.
  *A61K 9/00* (2006.01)
  *A61K 9/14* (2006.01)
  *A61K 31/07* (2006.01)
  *A61K 31/355* (2006.01)
  *A61K 31/593* (2006.01)

(52) U.S. Cl. ............ 424/442; 424/400; 424/439; 514/167; 514/458; 514/725; 514/904

(58) Field of Classification Search ......... 424/439, 424/400, 442; 514/167, 458, 725, 904
See application file for complete search history.

(56) References Cited

U.S. PATENT DOCUMENTS 3,932,634 A * 1/1976 Kardys
4,075,333 A * 2/1978 Josse
5,747,058 A * 5/1998 Tipton et al. ............ 424/423
6,162,419 A * 12/2000 Perricone et al.

* cited by examiner

Primary Examiner—Michael G. Hartley
Assistant Examiner—Simon J. Oh
(74) Attorney, Agent, or Firm—Connolly Bove Lodge & Hutz LLP

(57) ABSTRACT

A water-dispersible vitamin composition containing Vitamins A, D3 or E, or a precursor thereof, an alkyl lactate and an emulsifier and is substantially free of water.

26 Claims, No Drawings

CONCENTRATED WATER-DISPERSIBLE VITAMIN COMPOSITIONS

The present invention relates to new water-dispersible compositions to provide one or more of vitamins E, A and D₃ to an animal.

The present invention provides a water-dispersible liquid vitamin composition comprising:
a) from 40% to 90% by weight of a vitamin component selected from the group consisting of:
  (i) one or more precursors of Vitamin A;
  (ii) one or more precursors of Vitamin E;
  (iii) a mixture of one or more precursors of Vitamin A and one or more precursors of Vitamin E;
  (iv) a mixture of one or more precursors of Vitamin A and Vitamin D3;
  (v) a mixture of one or more precursors of Vitamin A and Vitamin D3; and
  (vi) a mixture of one or more precursors of Vitamin A, one or more precursors of Vitamin E, and Vitamin D3;
b) from 2% to 10% of a C1 to C6 alkyl lactate;
c) from 0% to 10% of a C2 to C6 mono-hydroxy alcohol;
d) from 5% to 50% of a one or more veterinarily acceptable emulsifiers; and
e) from 1% to 12% of an oil;
wherein the composition is substantially free of water.

Component a) of the composition may be from 45% to 85% by weight.

It should be understood that in the present specification and claims by the term "%" is meant percent by weight unless expressly noted otherwise.

In certain embodiments of the present invention, the liquid vitamin composition consists essentially of the ingredients listed in the foregoing description of the composition.

The vitamins are suitably provided as the oily derivative of the vitamin, such as the lower alkyl esters of the vitamin as a solution or suspension in an oil (e.g., a veterinarily acceptable oil). By the term lower alkyl is generally meant C1–C6 alkyl which is optionally substituted by one or more halogens. For example Vitamin A may be provided as retinyl propionate. Vitamin E may be provided as, e.g, (DL) alpha tocopheryl acetate. Suppliers of the vitamins or precursors thereof include Hoffman LaRoche Corporation, and Aventis Animal Nutrition. Such products are generally known to those skilled in the art.

The oil is, e.g., a fatty acid oil, such as a vegetable oil, as needed to provide the compositions. Such oils are acceptable as food additives and known to the person skilled in the art. Such oils include soybean oil, corn oil, canola oil, peanut oil and the like. In the case of vitamin E, or its precursor dl-alpha tocopheryl acetate, the oil may be composed of or include a manufacturing by-product.

In another aspect of the invention, the composition may further comprise from 0 to 5% of a stabilizer. The stabilizer enhances vitamin stability and keeps the composition as a flowable liquid for an extended period of time, generally from 1 to 6 months. The stabilizer may also function as an anti-gelling agent and/or as an antifreeze. Suitable stabilizers include propylene glycol, sorbitol and glycerine. The preferred agent is propylene glycol.

In another aspect of the invention, the ratio of the alkyl lactate to the alcohol is from 1:1 to 3:1, preferably from 1.5:1 to 2.8:1.

Examples of mono-hydroxy alcohols include ethanol, n-propanol or isopropanol. The mono-hydroxy alcohol is preferably a normal alcohol. Propanol is highly preferred. In one embodiment of the present invention, the amount of mono-hydroxy alcohol may be from about 2% to 5%, or from about 3% to 5%.

Alkyl lactates that may be used according to the invention include methyl lactate, ethyl lactate, n-propyl lactate, iso-propyl lactate, n-butyl lactate, iso-butyl lactate, sec-butyl lactate, tert-butyl lactate, n-pentyl lactate, n-hexyl lactate and other isomeric forms thereof. The alcohol portion of the ester may be optionally substituted by one or more halogens. Ethyl lactate and butyl lactate are examples of preferred alkyl lactates that are used in the invention. All enantiomeric and diasteromeric forms of lactate esters are embraced by the present invention. Lactate esters of L(+) lactic acid are generally preferred.

By the term substantially free of water may be meant less than 1%, or less than 0.5% or less than 0.1% by weight water in the composition.

The emulsifiers according to the present invention may be of any type of emulsifiers, and are preferably non-ionic surfactants. Examples of non-ionic surfactants include polyethylene glycol esters and ethoxylated sorbitan fatty acid esters. Examples of these groups of surfactants include Polysorbate 80, Polysorbate 80K, PEG 400, Alkamuls® PSMO-20, Alkamuls® 400-MO, T-MAZ 80K, MAPEG® 400Mo and the like and are generally known to those skilled in the art.

The compositions of the present invention may have viscosities that are from 1000 cP to 10000 cP at 0° C. and from 50 cP to 2000 cP at 10° C. It is understood that viscosities are measured by the Brookfield method known to those of skill in the art and specifically described in example 7 of this application.

Another aspect of the present invention is that the composition may be quickly dispersed in water. That is the composition adequately disperses into water within 2 minutes, preferably within 20 seconds, when added at a ratio of composition to water of from 1 g/kg to 100 g/kg, preferably from 3 to 10 g/kg. By the term "adequately disperses" is meant that the composition disperses into water and forms a finely dispersed emulsion (e.g., under the conditions specified in Example 6).

The composition may also comprise a fungicide. Any suitable fungicide acceptable in veterinary medicine may be used and in particular potassium sorbate is preferred. When a fungicide is used, it is present in the composition in trace amounts, for example, from about 0.05% to 0.3% by weight of the composition.

The concentration of each vitamin in the compositions may be varied to satisfy the specific requirements of the product desired. Generally, Vitamin A is present in an amount of from 800,000 to 1,200,000 IU/g, preferably from 800,000 to 1,000,000 IU/g. Vitamin D3 is generally present in an amount of from 50,000 to 1,200,000 IU/g, preferably from 100,000 to 1,000,000 IU/g. Vitamin E is generally present in an amount of from 100 to 1000 IU/g, preferably from 200 to 750 IU/g.

The specific products set forth in Table 1 are contemplated by the invention. Stock solutions or suspensions of vitamins and vitamin precursors are generally supplied at specific International potency units per/gram (IU/g). For example, the precursor to Vitamin A used in the formulations of Table 1 is retinyl propionate which is used as a 79% by weight solution of retinyl propionate dissolved in canola oil and stabilized with 1% by weight ethoxyquin. This means that the retinyl propionate/canola oil solution contains about 2,200,000 IU/g of Vitamin A (pure all trans retinyl propionate has a theoretical potency of 2,780,000 IU/g). The Vitamin D3 concentrate used in Table 1 is an oily concentrate prepared from Vitamin D3 resin and contains about 10% by weight Vitamin D3 in vegetable oil. The Vitamin D3/vegetable oil concentrate is stabilized with BHA or BHT and has about 4,000,000 IU/g of Vitamin D3 (pure cholecalciferol, also known as 1o Vitamin D3, has a theoretical potency of 40,000,000 IU/g). The Vitamin E precursor used in Table 1 is 94.5% by weight pure dl-alpha tocopheryl acetate in oil (945 IU/g).

TABLE 1

| Product Name | Vitamin | Precursor | Vitamin Potency (IU/g) | % weight of Vitamin or precursor | % weight oil |
|---|---|---|---|---|---|
| A1000 | A | Retinyl propionate | 1,000,000 | 38.7 | 10.3 |
| AD3 1000/200 | A | Retinyl propionate | 1,000,000 | 38.7 | 10.3 |
|  | D3 | None | 200,000 | 0.52 | 4.68 |
| AD3 1000/100 | A | Retinyl propionate | 1,000,000 | 38.7 | 10.3 |
|  | D3 | None | 100,000 | 2.34 | 0.26 |
| AD3E 800/200/200 | A | Retinyl propionate | 800,000 | 31.0 | 8.2 |
|  | D3 | None | 200,000 | 0.52 | 4.68 |
|  | E | dl alpha tocopheryl acetate | 200 | 20.6 | 1.2 |
| E60 | E | dl alpha tocopheryl acetate | 600 | 61.8 | 3.6 |
| E75 | E | dl alpha tocopheryl acetate | 750 | 77.3 | 4.5 |
| E80 | E | dl alpha tocopheryl acetate | 800 | 82.4 | 4.8 |

EXAMPLE 1

A composition containing the ingredients in Table 2 was prepared by sequentially adding, under agitation, 94.5% by weight pure dl-alpha tocopheryl acetate in oil, emulsifier (PEG 400), ethyl lactate and propanol and mixing until homogeneous (generally two hours).

TABLE 2

| Ingredient | Kilograms | Percent |
|---|---|---|
| 94.5% pure dl-alpha tocopheryl acetate (in oil) | 817.5 | 81.75 |
| PEG 400 | 82.5 | 8.25 |
| Ethyl Lactate | 70 | 7.0 |
| Propanol | 30 | 3.0 |
| Total | 1000 | 100 |

EXAMPLE 2

A composition containing the ingredients in Table 3 was prepared by the procedure of Example 1 where products were added sequentially under agitation and mixed until homogeneous.

TABLE 3

| Ingredient | Kilograms | Percent |
|---|---|---|
| Retinyl Propionate 79% in canola oil | 489.5 | 48.95 |
| Polysorbate 80 | 61.0 | 6.10 |
| PEG 400 MO | 339.5 | 33.95 |
| Ethoxyquin | 30.0 | 3.00 |
| Ethyl Lactate | 50.0 | 5.00 |
| Propanol | 30.0 | 3.00 |
| Total | 1000.0 | 100 |

EXAMPLE 3

A composition containing the ingredients in Table 4 was prepared by the procedure of Example 1 where products were added sequentially under agitation and mixed until homogeneous.

TABLE 4

| Ingredient | Kilograms | Percent |
|---|---|---|
| Retinyl Propionate 79% in canola oil | 489.5 | 48.95 |
| Vitamin D3 10% in oil | 26.3 | 2.63 |
| Polysorbate 80 | 30.0 | 3.00 |
| PEG 400 MO | 274.2 | 27.42 |
| Ethyl Lactate | 50.0 | 5.00 |
| BHT | 30.0 | 3.00 |
| Propanol | 100.0 | 10.00 |
| Total | 1000.0 | 100 |

EXAMPLE 4

A composition containing the ingredients in Table 5 was prepared by the procedure of Example 1 where products were added sequentially under agitation and mixed until homogeneous.

TABLE 5

| Ingredient | Kilograms | Percent |
|---|---|---|
| Vitamin D3 10% in oil | 52.5 | 5.25 |
| 94.5% pure dl-alpha tocopheryl acetate (in oil) | 218.0 | 21.8 |
| Retinyl Propionate 79% in canola oil | 391.6 | 39.16 |
| Polysorbate 80 | 37.9 | 3.79 |
| PEG 400 MO | 188.0 | 18.80 |
| Ethoxyquin | 30.0 | 3.00 |
| Ethyl Lactate | 50.0 | 5.00 |
| Propanol | 32.0 | 3.20 |
| Total | 1000.0 | 100 |

The viscosity of the composition was 1300 cP at 0° C. and 500 cP at 10° C. The composition adequately dispersed into water at 100 g/kg water at 20 degrees C.

EXAMPLE 5

A composition containing the ingredients in Table 6 was prepared by the procedure of Example 1 where products are added sequentially under agitation and mixed until homogeneous

TABLE 6

| Ingredient | Kilograms | Percent |
| --- | --- | --- |
| Vitamin D3 | 52.5 | 5.25 |
| Retinyl Propionate | 489.5 | 48.95 |
| Polysorbate 80 | 70.0 | 7.00 |
| PEG 400 MO | 276.0 | 27.60 |
| Ethoxyquin | 30.0 | 3.00 |
| Ethyl Lactate | 50.0 | 5.00 |
| Propanol | 32.0 | 3.20 |
| Total | 1000.0 | 100 |

The viscosity of the composition was 800 cP at 0° C. and 350 cP at 10° C. The composition adequately dispersed into water at 100 g/kg water at 20 degrees C.

EXAMPLE 6

About 5 drops (approx 0.15 g) of composition is added to 50 ml of water (room temperature which is from about 15° C. to about 25° C.) in a 100 ml flat-bottomed beaker and stirred with rod manually for 20 seconds. The resulting emulsion is examined and rated according to the following scale.

1. No emulsion or dispersion; composition is separated from water
2. Partial emulsion/dispersion but large agglomerations of test product are observed
3. Almost complete emulsion/dispersion; small agglomerations are visible
4. Complete emulsion/dispersion; homogeneous liquid without any visible agglomerations The compositions of Examples 1, 2, 3, 4 and 5 adequately dispersed into water at 100 g/kg water at 20° C.

EXAMPLE 7

Viscosity is measured with a Brookfield DV-II+Viscometer (Brookfield Engineering Labs, Middleboro, Mass.) using RV spindle #3. The composition to be tested was placed in a 200 ml flat-bottomed sample jar and chilled at −20° C. for several hours. The viscometer functions in combination with a microcomputer supplied by Brookfield and uses a timed-stop program whereby a viscosity reading was taken every 30 seconds. Viscosity, torque and temperature are measured until the sample warmed to about from 10° C. to 15° C.

The following viscosities were recorded:

| Example | Temp. A | Viscosity A | Temp B | Viscosity B |
| --- | --- | --- | --- | --- |
| 1 | 0° C. | 6000 cP | 10° C. | 1200 cP |
| 2 | 0° C. | 800 cP | 10° C. | 400 cP |
| 3 | 0° C. | 250 cP | 10° C. | 200 cP |
| 4 | 0° C. | 1300 cP | 10° C. | 500 cP |
| 5 | 0° C. | 800 cP | 10° C. | 350 cP |

It should be understood that the preceeding is merely a detailed description of the embodiments of the invention and that numerous changes to the disclosed embodiments can be made in accordance with the disclosure herein without departing from the spirit or scope of the invention. The preceding description, therefore, is not meant to limit the scope of the invention. Rather, the scope of the invention is to be determined only by the appended claims and their equivalents.

The invention claimed is:

1. A method for preparing a water-dispersible liquid vitamin food additive for animals, said food additive being substantially free of water, said method comprising the steps of:
   sequentially adding, under agitation,
   (a) from 61% to 90% by weight of a vitamin component in from 1% to 12% of an oil, said vitamin component being selected from the group consisting of:
      (i) one or more precursors of vitamin A,
      (ii) one or more precursors of vitamin E,
      (iii) a mixture of one or more precursors of vitamin A and one or more precursors of vitamin E,
      (iv) a mixture of one or more precursors of vitamin A and vitamin D3,
      (v) a mixture of one or more precursors of vitamin E and vitamin D3, and
      (vi) a mixture of one or more precursors of vitamin A, one or more precursors of vitamin E and vitamin D3;
   (b) one or more veterinarily acceptable emulsifiers;
   (c) from 2% to 10% of a C1 to C6 alkyl lactate;
   (d) from 2% to 10% of a C2 to C6 mono-hydroxy alcohol; and mixing until homogeneous.

2. The method of claim 1, further comprising up to 5% of a stabilizer, said stabilizer being added after the emulsifier (b) is added and before the alkyl lactate (c) is added, or after the alkyl lactate (c) is added and before the mono-hydroxy alcohol (d) is added.

3. The method of claim 2, wherein the ratio of the alkyl lactate (c) to the mono-hydroxy alcohol (d) is from 1:1 to 3:1.

4. The method of claim 3, wherein the ratio of the alkyl lactate (c) to the mono-hydroxy alcohol (d) is from 1.5:1 to 2.8:1.

5. The method of claim 1, wherein the one or more emulsifiers (b) is a non-ionic surfactant selected from the group consisting of polyethylene glycol esters and ethoxylated sorbitan fatty esters.

6. The method of claim 1, wherein the alkyl lactate (c) is selected from the group consisting of methyl lactate, ethyl lactate, n-propyl lactate, iso-propyl lactate, n-butyl lactate, sec-butyl lactate, tert-butyl lactate, n-pentyl lactate, n-hexyl lactate and other isomeric forms thereof.

7. The method of claim 1, wherein the oil of component (a) is a vegetable oil selected from the group consisting of soybean oil, corn oil, canola oil and peanut oil.

8. The method of claim 1, wherein the component (a) is dl-alpha-tocopheryl acetate in oil.

9. The method of claim 1, wherein the component (a) is the retinyl propionate in canola oil.

10. The method of claim 1, wherein the component (a) is the retinyl propionate in canola oil and the vitamin D3 in oil.

11. The method of claim 1, wherein the component (a) is the vitamin D3 in oil, the dl-alpha-tocopherol in oil and retinyl propionate in canola oil.

12. The method of claim 1, wherein the viscosity of the food additive is from 1000 cP to 10,000 cP at 0° C.

13. The method of claim 1, wherein component (b) is added in an amount from 5% to 50% of one or more veterinarily acceptable emulsifiers.

14. The method of claim 1, wherein from 61% to 82% by weight of said vitamin component is added.

15. The method of claim 1, wherein from 61% to 77% by weight of said vitamin component is added.

16. The method of claim 1, wherein from 77% to 82% by weight of said vitamin component is added.

17. The method of claim 1, wherein from 61% to 85% by weight of said vitamin component is added.

18. The method of claim 1, wherein from 77% to 85% by weight of said vitamin component is added.

19. The method of claim 1, wherein 61% by weight of said vitamin component is added.

20. The method of claim 1, wherein 77% by weight of said vitamin component is added.

21. The method of claim 1, wherein 82% by weight of said vitamin component is added.

22. A method for dispersing a water-dispersible liquid vitamin food additive for animals, said food additive being substantially free of water, said method comprising the steps of:
   preparing the food additive by sequentially adding, under agitation,
   (a) from 61% to 90% by weight of a vitamin component in from 1% to 12% of an oil, said vitamin component being selected from the group consisting of:
      (i) one or more precursors of vitamin A,
      (ii) one or more precursors of vitamin E,
      (iii) a mixture of one or more precursors of vitamin A and one or more precursors of vitamin E,
      (iv) a mixture of one or more precursors of vitamin A and vitamin D3,
      (v) a mixture of one or more precursors of vitamin E and vitamin D3, and
      (vi) a mixture of one or more precursors of vitamin A, one or more precursors of vitamin E, and vitamin D3;
   (b) one or more veterinarily acceptable emulsifiers;
   (c) from 2% to 10% of C1 to C6 alkyl lactate;
   (d) from 2% to 10% of a C2 to C6 mono-hydroxy alcohol; and mixing until homogeneous; and
   dispersing said food additive into water within 2 minutes when added at a ratio of said food additive to water from 1 g/kg to 100 g/kg.

23. The method of claim 22, comprising dispersing said food additive into water within 20 seconds when added at a ratio of said food additive to water from 1 g/kg to 100 g/kg.

24. The method of claim 22, wherein component (b) is added in an amount from 5% to 50% of one or more veterinarily acceptable emulsifiers.

25. A method for dispersing a water-dispersible liquid vitamin food additive for animals comprising the step of dispersing a food additive prepared according to the method of claim 1 into water within two minutes when added at a ratio of said food additive to water of from 1 g/kg to 100 g.kg.

26. The method of claim 25, comprising dispersing said food additive into water within 20 seconds when added at a ratio of said food additive to water from 1 g/kg to 100 g/kg.

* * * * *

UNITED STATES PATENT AND TRADEMARK OFFICE
CERTIFICATE OF CORRECTION

| | | |
|---|---|---|
| PATENT NO. | : 7,081,248 B2 | Page 1 of 1 |
| APPLICATION NO. | : 09/920365 | |
| DATED | : July 25, 2006 | |
| INVENTOR(S) | : Michel A. Crepeau | |

It is certified that error appears in the above-identified patent and that said Letters Patent is hereby corrected as shown below:

In Claim 25, at column 8, line 26, "g.kg" should read -- g/kg --

Signed and Sealed this

Third Day of April, 2007

JON W. DUDAS
*Director of the United States Patent and Trademark Office*